United States Patent
Vishnia et al.

(10) Patent No.: US 8,079,981 B2
(45) Date of Patent: **\*Dec. 20, 2011**

(54) DEVICE FOR HEATING A FLOW OF LIQUID BY ELECTRICAL HEATING OF A METALLIC CONDUIT

(75) Inventors: David Vishnia, Raanana (IL); Eyal Shani, Gan Yeshaya (IL); Ron Elazari-Volcani, Rehovot (IL); Avner Kaidar, Haifa (IL)

(73) Assignee: Quality In Flow Ltd., Petach Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/870,824

(22) Filed: Aug. 29, 2010

(65) Prior Publication Data

US 2010/0320186 A1    Dec. 23, 2010

Related U.S. Application Data

(63) Continuation-in-part of application No. PCT/IL2008/000362, filed on Mar. 13, 2008, and a continuation-in-part of application No. 11/685,234, filed on Mar. 13, 2007, now Pat. No. 7,846,130.

(51) Int. Cl.
*A61F 7/12*    (2006.01)
(52) U.S. Cl. ...................................... 604/114
(58) Field of Classification Search ............... 604/114
See application file for complete search history.

(56) References Cited

U.S. PATENT DOCUMENTS

| | | | | |
|---|---|---|---|---|
| 4,038,519 | A | * | 7/1977 | Foucras ........................ 392/472 |
| 4,707,587 | A | * | 11/1987 | Greenblatt .................... 392/466 |
| 6,142,974 | A | * | 11/2000 | Kistner et al. ................. 604/113 |
| 2008/0058697 | A1 | * | 3/2008 | Kamen et al. ................ 604/6.13 |
| 2008/0077087 | A1 | * | 3/2008 | Martens ........................ 604/113 |
| 2008/0281268 | A1 | * | 11/2008 | Vest Hansen ................. 604/114 |

* cited by examiner

*Primary Examiner* — Nicholas Lucchesi
*Assistant Examiner* — Jason Flick
(74) *Attorney, Agent, or Firm* — Mark M. Friedman (57) ABSTRACT

A device (100) for heating a flow of liquid from an initial temperature to a desired temperature for intravenous delivery includes an elongated conduit (120) formed from metallic material having an inlet (102) for receiving the flow of liquid at the initial temperature and an outlet (104) for delivering the flow of liquid at the desired temperature. A temperature sensing arrangement (160. 162, 224) is deployed to generate an output indicating the temperature of the liquid at a number of locations along the conduit (120). A controller (140) generates electrical current flowing within at least one length of the wall of the conduit, thereby generating heat within the wall so as to heat the flow of liquid to reach the desired temperature at the outlet.

21 Claims, 6 Drawing Sheets

DEVICE FOR HEATING A FLOW OF LIQUID BY ELECTRICAL HEATING OF A METALLIC CONDUIT

This application is a Continuation-in-Part of PCT/IL2008/000362 filed Mar. 13, 2008 and of pending U.S. patent application Ser. No. 11/685,234 filed Mar. 13, 2007.

FIELD AND BACKGROUND OF THE INVENTION

The present invention generally relates to a device for heating a flow of liquid. More specifically, the present invention relates to a device for heating a flow of liquid, particularly from intravenous delivery, by generation of an electrical current within the wall of a metallic conduit through which the liquid flows.

By way of introduction, and as an example, fluids that are administered intravenously to a patient include blood-based fluids and non-blood fluids, collectively referred to herein as "intravenous (IV) fluids". While awaiting use, blood-based fluids are maintained in cool storage at approximately 4° C., and in the case of certain blood products frozen. Non-blood fluids are usually stored at room-temperature.

In extreme environmental conditions when the human body is exposed to cold temperatures, its internal mechanisms may be unable to replenish the heat that is being lost to the body's surroundings. Hypothermia occurs commonly in trauma, environmental exposure, and during major operative procedures. It is well known that hypothermia poses a significant risk to patients. Administration of unheated, or insufficiently heated, intravenous fluids, can cause substantial heat loss and can cause, or at least contribute to, serious patient hypothermia problems, hence aggravating the patient's condition. In addition, unintended hypothermia can be a risk during each operation, and care must be taken during surgery to keep the patient at a normal body temperature.

In the art, it is known that IV fluids need to be warmed prior to intravenous administration. However, care must be exercised; overheating IV fluids, especially blood-based compositions, could destroy the constituents of the blood, and endangers the patient's life. Examples of method and convection systems for heating IV fluids are disclosed in U.S. Pat. No. 4,707,587 and U.S. Pat. No. 5,106,373. A heat exchanger may also be employed for keeping the temperature of the IV fluid constant. Unfortunately, this possesses the disadvantage of requiring a large amount of fluid and of increasing the overall size of the apparatus. It is also possible to surround the medical tube carrying the IV fluid with heating elements. It is noted that such heating fluid systems have been described in several patent documents, including U.S. Pat. No. 1,995,302; U.S. Pat. No. 4,038,519; and U.S. Pat. No. 3,355,572 each of which is incorporated by reference in its entirety. U.S. Pat. Nos. 1,995,302 and 4,038,519 feature a flexible tube suitable for medical uses in which heating is provided by means of wires or strips of a resistive heating conductor embedded in a helical fashion within the walls of the tubing. U.S. Pat. No. 3,355,572 discloses composite tubing in which heating wires are wound spirally around the inner layer of the tubing and are embedded in the outer layer of the tubing.

While some of the above-mentioned devices are appropriate for their particular uses, they tend to heat in non-gradual increasing temperature, resulting in localized hotspots and overheating of the fluid in the conduit. While this effect may be inconsequential in certain applications, it is problematic when heating an IV fluid, such as blood. Since the properties of the blood may be degraded at temperatures of about 49° C., a localized hotspot may result in significant degradation of the blood. Because blood must be heated to a regulated set temperature (about 37° C.) to achieve optimal results, the conduit must be capable of heating blood uniformly and maintaining its temperature within a narrow range.

Moreover, in order for a bulk warmer to be constantly ready for emergency use, it must be maintained at a proper and set temperature. This requires a system which is bulky, heavy, and/or fixed. The use is impracticable under field emergency conditions, in situations such as military field conditions, pre-hospital treatment such as air rescue flight or ambulance conditions or out-patients environment conditions. In the hospital operating room, a compact size warmer would also be advantageous over regular warmers, being easily transported within the operating room, between operating rooms, or in the hospital. A compact size would also free up precious space next to the operating table for other medical devices.

U.S. Pat. No. 6,142,974 to Kistner et al. discloses a networked tube containing parallel straight sections in the same plane, wrapped (encapsulated) in a flexible material which supports resistive heating elements. Unfortunately, in the above-mentioned system fluid leakage often occurs due to the discontinuity of the conduit.

An alternative approach is proposed by U.S. Pat. No. 5,713,864 to Verkaart in which biological fluids are heated by a resistive polymer strip integrated into the structure of a polymer tube through which the fluid is flowing. This approach is promising due to the relatively uniform heating effect along the length of the tube. However, the use of conductive polymers as the heating element is energetically inefficient and requires high actuating voltages, which may pose a safety risk for medical IV applications. Furthermore, since the polymer materials are relatively poor thermal conductors, it is generally not feasible to measure the temperature of the fluid flowing through the tube without compromising the sealing of the tube by insertion of a temperature sensing element directly into the flow path.

Therefore, there is an ongoing need for a safe and compact fluid heating device which could be used under a wide range of environmental conditions capable of transporting and warming fluids for intravenous infusion at a continuously regulated desired temperature, thereby preventing hypothermia.

SUMMARY OF THE INVENTION

The present invention is a device for heating a flow of liquid, particularly from intravenous delivery, by generation of an electrical current within the wall of a metallic conduit through which the liquid flows.

According to the teachings of the present invention there is provided, a device for heating a flow of liquid from an initial temperature to a desired temperature for intravenous delivery, the device comprising: (a) an elongated conduit formed from metallic material, the conduit having an inlet for receiving the flow of liquid at the initial temperature and an outlet for delivering the flow of liquid at the desired temperature; (b) at least one temperature sensing arrangement associated with the conduit and deployed to generate an output indicative of a temperature of the liquid at least one location along the conduit; and (c) a controller associated with the temperature sensing arrangement and deployed for generating electrical current flowing within at least one length of the wall of the conduit, thereby generating heat within the wall so as to heat the flow of liquid to reach the desired temperature at the outlet.

According to a further feature of the present invention, the at least one temperature sensing arrangement includes a temperature responsive element positioned in thermal contact with an external surface of the conduit.

According to a further feature of the present invention, the conduit has a minimum wall thickness of no more than about 1.4 mm.

According to a further feature of the present invention, the conduit has a minimum wall thickness of no more than about 0.4 mm.

According to a further feature of the present invention, the conduit is formed a material having a thermal conductivity of at least about 5 W/(m.K).

According to a further feature of the present invention, the conduit has an electrical resistance of no more than about 15 ohms.

According to a further feature of the present invention, the conduit has an electrical resistance of no more than about 5 ohms.

According to a further feature of the present invention, the conduit is formed primarily from stainless steel.

According to a further feature of the present invention, the controller is deployed for generating a first electrical current flowing within a first length of the wall of the conduit and a second electrical current flowing within a second length of the wall of the conduit.

According to a further feature of the present invention, the fluid flow from the inlet to the outlet passes sequentially through the first length and the second length, and wherein the at least one temperature sensing arrangement is deployed to generate an output indicative of a temperature of the liquid: (a) in proximity to a transition from the first length to the second length; and (b) after flowing through the second length.

According to a further feature of the present invention, the controller is configured to generate the first current so as to heat the fluid flow passing along the first length through a major part of a temperature difference between the initial temperature and the desired temperature, and to generate the second current so as to heat the fluid flow passing along the second length through a remaining temperature correction to achieve the desired temperature at the outlet.

According to a further feature of the present invention, the first length and the second length of the conduit are interconnected by an intermediate section of the conduit, and wherein the at least one temperature sensing arrangement includes a temperature responsive element positioned in thermal contact with an external surface of the intermediate section.

According to a further feature of the present invention, the temperature sensing arrangement includes a temperature responsive element deployed within the liquid flow in proximity to the outlet.

According to a further feature of the present invention, the conduit includes an internal coating of an electrically insulating layer.

According to a further feature of the present invention, the conduit is provided with a thermally insulating covering over a major portion of its surface.

According to a further feature of the present invention, the conduit, the at least one temperature sensing arrangement and the controller are included within a portable housing.

According to a further feature of the present invention, the housing further includes a battery associated with the controller and configured to allow operation of the device without connection to an external power supply.

According to a further feature of the present invention, the controller is implemented as a reusable device, and wherein at least the conduit is implemented as a single-use interchangeable element.

According to a further feature of the present invention, there is also provided a flow meter associated with the controller and operative to measure a rate of the fluid flow through the conduit.

According to a further feature of the present invention, there is also provided a flow pump associated with the controller and operative to generate a desired rate of the fluid flow through the conduit.

According to a further feature of the present invention, there is also provided a flow shut-off valve associated with the controller and deployed to selectively shut off flow through the conduit.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the scope of the invention as defined by the appended claims.

BRIEF DESCRIPTION OF THE DRAWINGS

The invention is herein described, by way of example only, with reference to the accompanying drawings, wherein.

DESCRIPTION OF THE PREFERRED EMBODIMENTS

The following description is provided, together with the drawings, so as to enable any person skilled in the art to make use of said invention and sets forth the best modes contemplated by the inventor of carrying out this invention. Various modifications, however, will be apparent to those skilled in the art in view of the general principles of the present invention as described.

Thus, in general terms, the present invention is a device, generally designated 100, constructed and operative according to the teachings of the present invention, for heating a flow of liquid from an initial temperature to a desired temperature for intravenous delivery. Generally speaking, device 100 includes an elongated conduit 120, formed from metallic material, having an inlet 102 for receiving the flow of liquid at the initial temperature and an outlet 104 for delivering the flow of liquid at the desired temperature. At least one temperature sensing arrangement (described below) is associated with conduit 120 and deployed to generate an output indicative of a temperature of the liquid at one or more location along the conduit. A controller 140, associated with the temperature sensing arrangement, is deployed for generating electrical current flowing within at least one length of the wall of conduit 120, thereby generating heat within the wall so as to heat the flow of liquid to reach the desired temperature at outlet 104.

At this stage, it will already be apparent that the present invention provides profound advantages over the aforementioned devices of the prior art. Firstly, the use of electrical heating by current flowing within the wall of conduit 120 ensures gradual and controlled heating of the flow of liquid. At the same time, the use of a metallic conduit allows the use of relatively low operating voltages important for safety, and facilitates accurate through-the-wall sensing of the liquid temperature due to the thin wall thickness and high thermal conductivity of the metallic material, thereby providing profound advantages compared to the conductive polymer implementations of the Verkaart reference as discussed above. These and other advantages of the present invention will become clearer from the following detailed description.

Before addressing the features of the present invention in more detail, it will be useful to define certain terminology as used herein in the description and claims. In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

The term 'plurality' applies hereinafter to any integer greater than or equal to one.

The term 'about' refers hereinafter to a range around the defined measure of no more than ±20%, unless a different degree of precision is specifically or implicitly required.

The term 'regulated normal body temperature' refers hereinafter to the body temperature of about 37° C. In this context, "about" refers to a temperature difference within 0.2° C.

The term "metallic" is used to refer to any metal or metal alloy. The term "stainless steel" is used to refer to any of a range of ferrous alloys with a minimum of 10.5% chromium content.

The phrase 'temperature sensing arrangement' refers hereinafter to any arrangement configured to measure the temperature of at least one predetermined location. In each implementation of a temperature sensing arrangement, an element deployed in thermal contact with the predetermined location to enable measurement of the temperature is referred to as a 'temperature responsive element'. Examples of a temperature responsive element include, but are not limited to, thermometers, thermocouples, temperature sensitive resistors (thermistors and resistance temperature detectors), bi-metal thermometers, semiconductor thermometers, quartz thermometers, fiber optics thermometers and ultrasonic thermometers.

Figure 1:
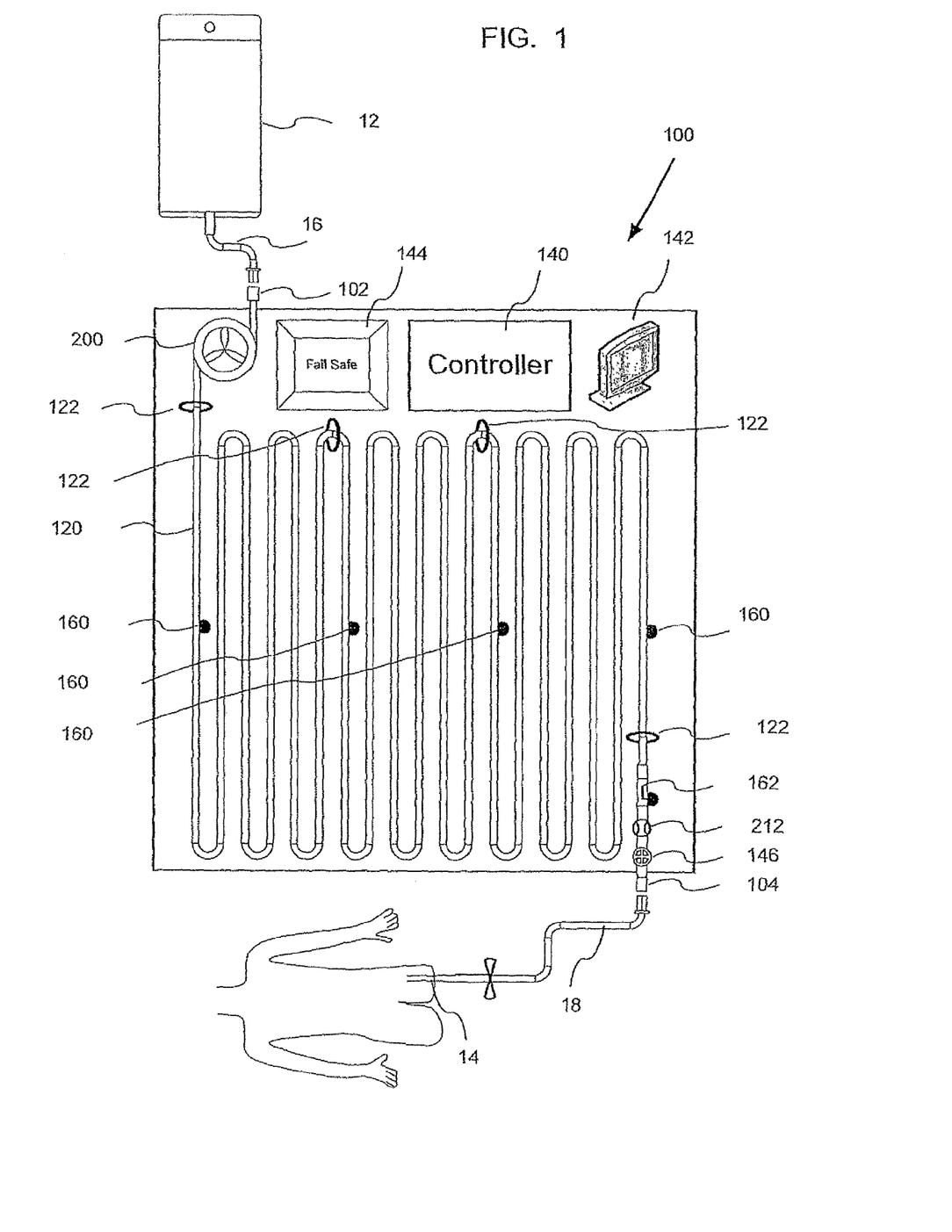
FIG. 1 is a schematic representation of a device, constructed and operative according to the teachings of the present invention, for heating a flow of liquid flowing from an infusion bag to a point of infusion into a patient's body.

Turning now again to the drawings, reference is made to FIG. 1 presenting a schematic and generalized illustration of device 100. Inlet 102 is preferably provided with a connector for connection to a tube 16 which transports the unwarmed fluid flow from an infusion bag 12. Outlet 104 is preferably provided with a connector for connection to a tube 18 which transports the warmed fluid flow to the patient's infusion point 14. Tubes 16 and 18, and the connectors may be implemented as any desired type of connectors and tubes suited to the intended use, and are typically components of standard medical infusion sets. Preferably, device 100 is adapted to be connected to a plurality of different commercially available infusion tube ports.

According to one embodiment of the present invention, device 100 further includes a display (screen) 142 for displaying and monitoring of system parameters and also for visual system alerts.

According to one embodiment of the present invention, device 100 further includes a flow shut-off valve 146 deployed to selectively shut off flow through conduit 120. Shut-off valve 146 may be electrically operated by connection to controller 140, either on occurrence of an error state indicating a malfunction of the device (e.g., flow blockage or reduction, overheating or the like), or in response to operation of a manually actuated failsafe button 144. In either case, controller 140 stops the flow of fluid and interrupts warming of the fluid. Additionally, or alternatively, a directly manually operated shut-off valve may be provided.

According to one embodiment of the present invention, device 100 further includes an audio alarm associated with controller 140 for providing audible alert signals on occurrence of a malfunction.

Figure 2:
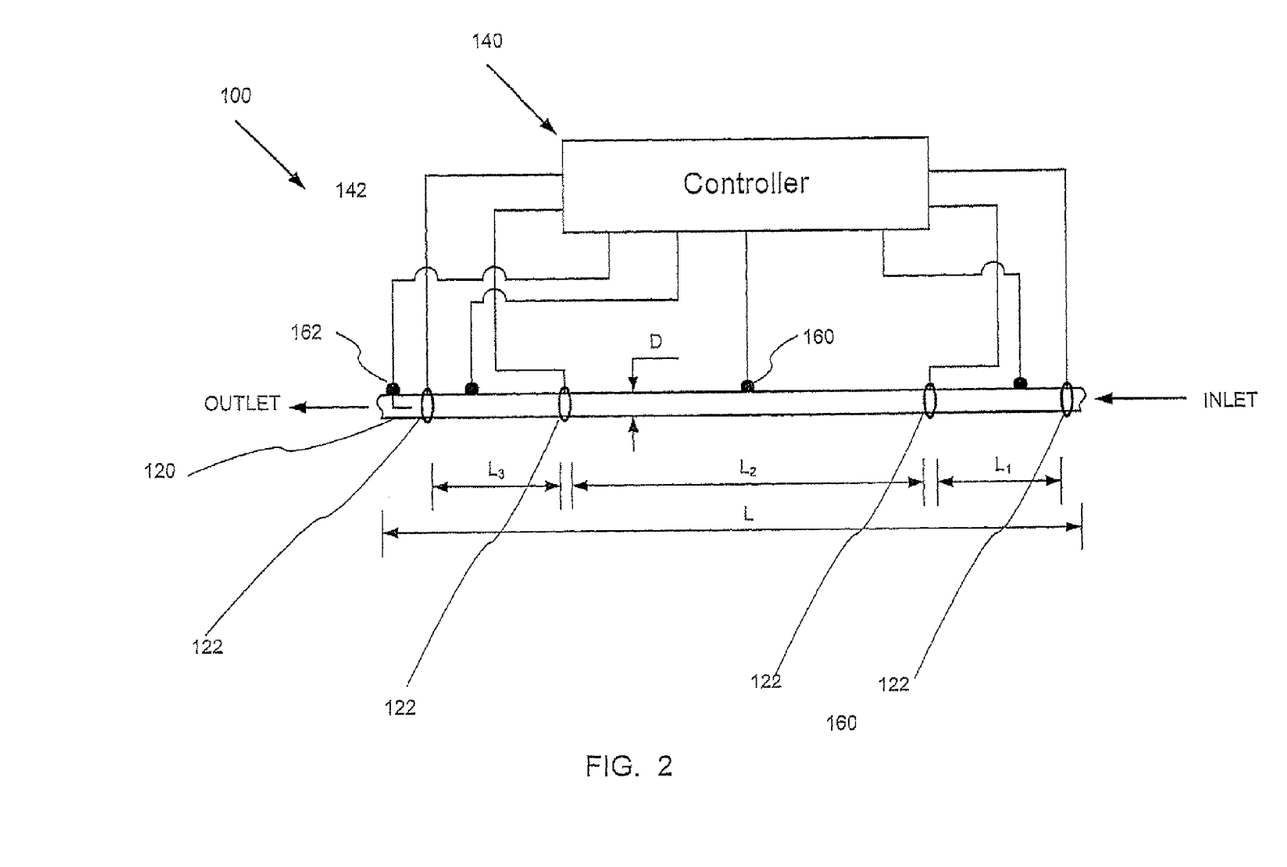
FIG. 2 is a schematic partial cross-sectional view of the device of FIG. 1 showing several applied voltage terminals, and several temperature sensors, used by a controller unit to monitor the temperature of the device and regulate an applied voltage at some or all of the terminals of the fluid heating device.

Reference is made now to FIG. 2 presenting a schematic and generalized illustration of the aforementioned portable device 100. Device 100 includes heated conduit 120, formed from a metallic material, especially designed for warming and transporting fluids, and controller 140 including a power source operative to heat the flowing fluid from one or more infusion bags from an initial temperature (for example, a storage temperature of about 4° C.) to a desired temperature, for example, normal body temperature. The temperature setting for normal body temperature is about 37° C., although, in certain specific applications of IV use, temperatures up to as high as 49° C. may be desired. Heated conduit 120 is operative as a resistive heater when an electric potential is applied along part or all of its length by controller 140. In a first preferred embodiment, the electric voltage is applied to terminals 122 near the extremities of conduit 120. In an alternative preferred embodiment, more than two voltage terminals 122 are distributed along the length L of conduit 120, and controller 140 applies voltages independently between neighboring terminals 122. This allows control over the heating profile along the length of conduit 120, for example, allowing relatively rapid heating of the liquid flow from the initial temperature to near the desired temperature along a first length of the conduit followed by a more precise fine temperature adjustment along a subsequent second length of the flow path. The subdivision into independently controlled sections of conduit is also valuable for allowing compensation for temporal variations in the temperature of the liquid flow entering inlet 102. Temperature responsive elements 160, forming part of the temperature sensing arrangement, are preferably installed between the voltage terminals so as to sense the temperature in each section length $L_1, L_2, \ldots, L_i$ of conduit 120, and most preferably, in proximity to a transition between each heated length and the next, and in proximity to the end of the last length. Optionally, in order to minimize any potential temperature measurement error due to heat generated within the wall of the conduit, the temperature responsive element may be positioned in thermal contact with an external surface of a non-heated intermediate section which interconnects adjacent heated lengths of the conduit.

In certain preferred embodiments, device 100 is a portable device suitable for use in emergency situations, field hospitals or the like. For such implementations, device 100 is preferably implemented as a free-standing device for use without requiring connection to an outside power source. Power for heating the liquid flow is preferably provided by an internal power source, such as a rechargeable battery or a fuel cell, implemented as part of controller 140. The power source is preferably rechargeable by connection to the power supply of a vehicle/aircraft/ship, or the electric power mains, or through a manual recharger. In the case of a fuel cell, the fuel is preferably readily replenishable by replacement of a fuel cartridge or the like.

In one non-limiting but preferred set of examples, the length L of conduit 120 is in the range of about 1 m to about 6 m, preferably in the range of about 3 m to about 5 m; the diameter D of conduit 120 is in the range of about 0.8 mm to about 8 mm, preferably about 2.8 mm and the thickness of the conduit wall is in the range of about 0.05 mm to about 1.4 mm, and most preferably in the range of about 0.1 mm to about 0.4 mm. Clearly, these ranges of wall thickness are much thinner than can be achieved using polymer materials, thereby rendering the device relatively compact. Furthermore, the metallic material of the conduit preferably has a thermal conductivity greater than 5 W/(m.K), and typically greater than 10 W/(m.K). The combination of low wall thickness and high thermal conductivity allows highly accurate through-the-wall temperature metering.

According to one embodiment of the present invention conduit 120 is a medical grade stainless steel tube. One of the advantages of this type of conduit is that it avoids some of the thermal degradation associated with heating. The term "thermal degradation" refers to an overheating of the conduit, due for example to the activation of the device that includes air instead of fluid, in which the conduit is able to be melted or to release unwanted substances into the liquid flow.

Moreover, conventionally available polymer tubes have an extremely low ability to transfer heat as defined by their respective thermal conductivity between 0.12 and 0.42 W/(m.K) while a conduit formed from a stainless steel tube having a higher thermal conductivity typically in excess of 10 W/m.K is a much better heat conductor.

Another advantage of this type of conduit is the durable and stable characteristics of the material under extreme environmental conditions, such as frost, humidity, heat, exposure to sunlight. Conduit 120 may also be stored for extended periods without altering its characteristics.

The length and the thickness of metallic conduit 120 are especially designed to provide a continuous gradual uniform accurate heating as well as high energy efficiency throughout the internal surface of conduit 120. Due to the high thermal conductivity of conduit 120, the heat efficiency is provided by the transfer from the thickness of the wall of conduit 120 to its internal surface which is in direct contact with the liquid flow. The high heat efficiency ensures minimal energy consumption. Energy efficiency is preferably further enhanced by provision of a thermally insulating covering over a major portion of the outer surface of conduit 120. The insulating covering is typically formed as a sleeve surrounding the conduit with openings where required for connection of electrical connections and temperature responsive elements.

According to certain preferred embodiments of the present invention, the inner surface of conduit 120 is coated with an electrically insulating material. The coating is made of a biologically compatible material. The thickness of the coating is minimal (typically a few tenths of a millimeter) in order to minimally degrade the heat transfer characteristics of the metallic conduit.

According to certain preferred embodiments of the present invention, conduit 120 may be disposable and able to be disconnected from controller 140 and replaced, allowing reuse of the more expensive controller while the components coming in contact with the liquid flow are disposable to ensure sterility for each use. Alternatively, conduit 120 may be reusable. In this case, conduit 120 is still preferably detachable to facilitate sterilization of the conduit without damage to controller 140.

Controller 140 also includes a temperature sensing arrangement operative to measure the temperature or temperatures of the fluid flowing inside conduit 120. The temperature sensing arrangement is preferably a high resolution system providing an indication of the measured temperatures to a precision of at least a fraction of a tenth of a degree Celsius. Based on these measurements, controller 140 preferably provides accurate control of the fluid flow outlet temperature settable with a resolution of at least about 0.1° C. and regulated to a precision significantly greater than the settable resolution over a wide range of flow rates. In certain preferred embodiments, the temperature sensing arrangement includes temperature responsive elements 160 deployed on the external surface of conduit 120 to sense the temperature of conduit 120. As discussed above, the properties of conduit 120 are such that the temperature of the external surface of conduit 120 is almost identical to the temperature of the internal wall of conduit 120. If even the small temperature differential between the liquid and the outside of the conduit is considered problematic, a correction can be calculated, based in part on information about the current flow rate. Optionally, another temperature responsive element 162 may be deployed within the liquid flow in proximity to outlet 104, thereby verifying the final temperature of the fluid before its introduction to the patient.

Figure 3:
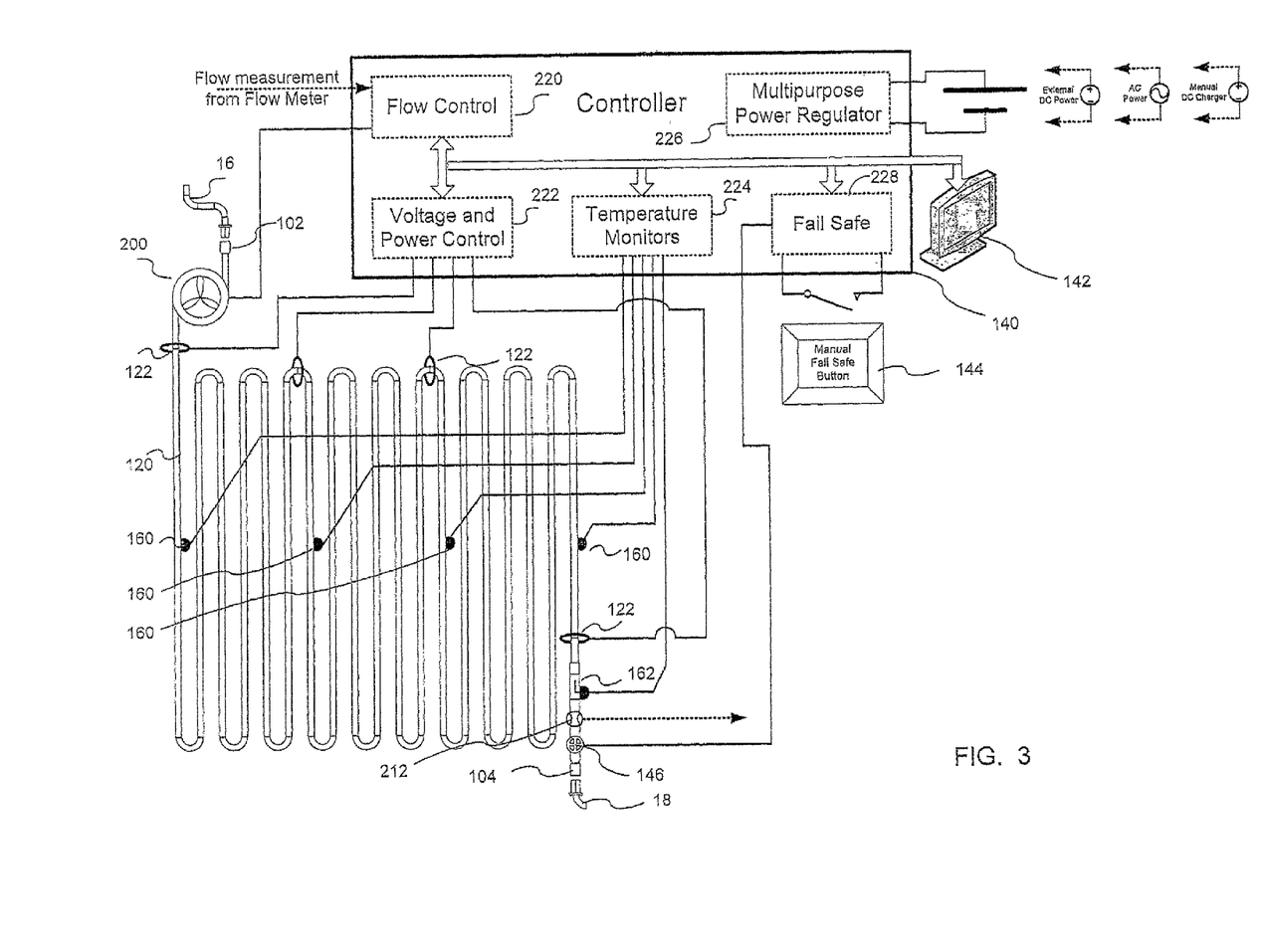
FIG. 3 and FIG. 4 are schematic illustrations of the controller block diagram showing, respectively, two different layouts of the heating tube, and further illustrating aspects of a fluid flow control and measurement arrangement.
Figure 4:
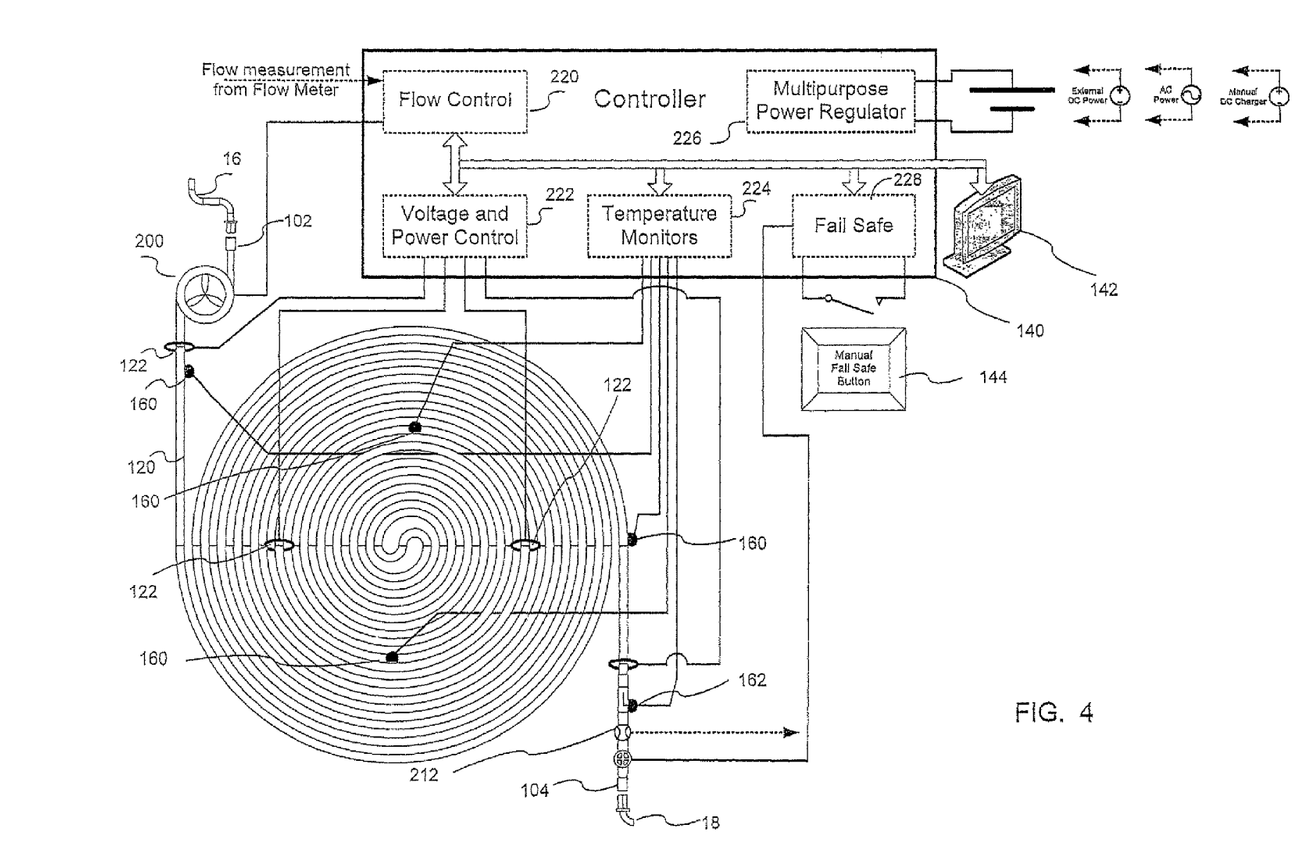

Turning now to FIGS. 3 and 4, these show additional schematic representations of device 100 illustrating certain additional optional features. The versions of FIGS. 3 and 4 differ primarily in the compact form used for conduit 120 in order to facilitate efficient packaging. In FIG. 3, there is shown a grid of parallel tube sections in which the flow path passes to and fro. FIG. 4, on the other hand, has conduit 120 implemented as a double spiral form. Both of these forms may be implemented using standard equipment for forming and shaping fine tubing and, once formed, are stable and self-supporting.

Figure 6:
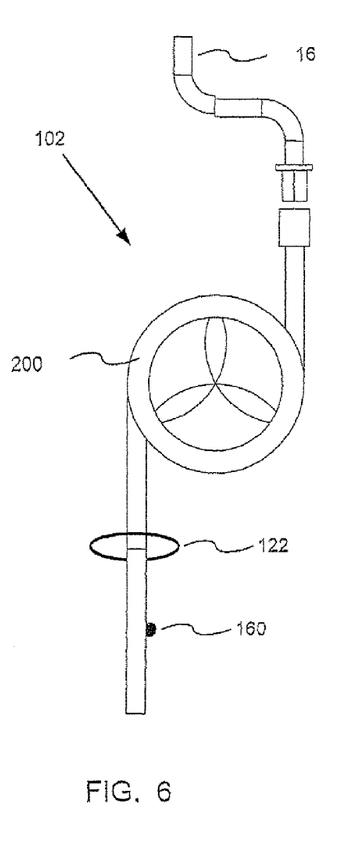
FIG. 6 is a schematic partial cross-sectional view of the handling parts at the fluid input section of the heating device showing a tube-connecting adapter to the external fluid, a flow pump, an applied voltage terminal and a temperature sensor.
Figure 7:
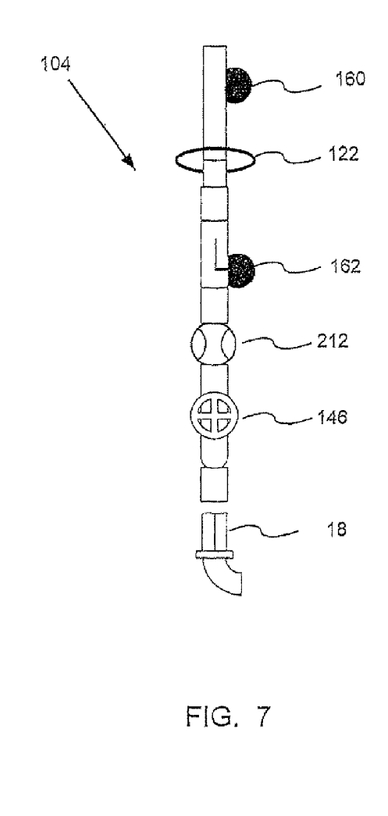
FIG. 7 is a schematic partial cross-sectional view of the handling parts at the fluid output section of the heating device showing a tube-connecting adapter to the external fluid, a failsafe valve, a flow sensor, an in-flow temperature sensor, an applied voltage terminal and a temperature sensor.

Also illustrated in FIGS. 3 and 4 are additional preferred features associated with inlet 102 and outlet 104 which are illustrated in more detail in FIGS. 6 and 7, respectively. Referring to FIG. 6, associated with inlet 102 are preferably a pump 200 for generating a desired rate of the fluid flow through conduit 120, an electrical connection 122 for application of a heating voltage from controller 140, and a temperature responsive element 160. Referring to FIG. 7, associated with outlet 104 are preferably a temperature responsive element 160, an electrical connection 122 for application of a heating voltage from controller 140, an additional submersed temperature responsive element 162, a flow sensor 212 for measuring a rate of fluid flow through conduit 120, and a flow interrupting valve 146.

FIGS. 3 and 4 also show further details of an exemplary implementation of controller 140. It should be noted that controller 140 may be implemented using a general purpose processing system including one or more processor operating under suitable software, or as dedicated hardware, firmware or any combination thereof, all in combination with various other peripheral hardware for interacting with other components of device 100, all as will be clear to one ordinarily skilled in the art. Furthermore, the various functions attributed to controller 140 may be subdivided between two or more separate units, all as a matter of design choice. Additional functional components of controller 140 illustrated in FIGS. 3 and 4 include a flow control module 220 for receiving output from flow meter 212 and actuating flow pump 200, a voltage and power control module 222 for applying the required voltages to terminals 122, temperature monitors module 224 for interacting with temperature responsive elements 160, 162 to provide the temperature sensing arrangement, a multipurpose power regulator 226 for managing battery charging and/or power input from various types of power source, and a failsafe module 228 for detecting various malfunction conditions and/or operation of manual failsafe button 144 and to actuate cut-off valve 146 and deactivate heating.

Controller 140 preferably monitors the fluid temperature at least three locations deployed throughout conduit 120, thereby safely monitoring the fluid temperature in device 100. In one non-limiting example, the device may be set to deliver fluid at a temperature selected in the range 38-39° C., for example, during treatment of hypothermia.

Figure 5A:
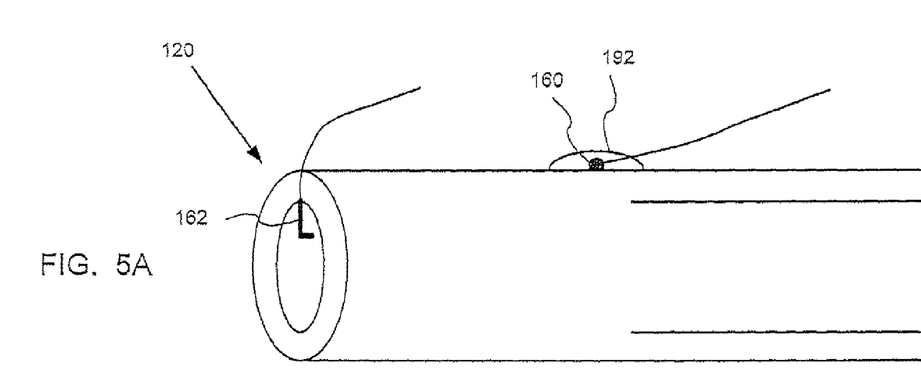
FIGS. 5A and 5B are schematic partial cross-sectional views of the heating conduit illustrated with and without an internal electrical insulation, respectively.
Figure 5B:
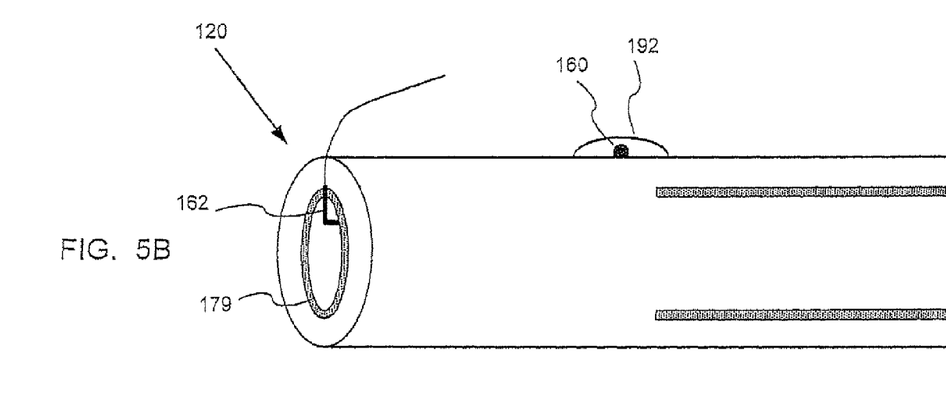

Reference is made now to FIGS. 5A and 5B which show schematic detailed views of the aforementioned conduit 120. A temperature responsive element 160 deployed on the external surface of conduit 120 measures the temperature of conduit 120. Temperature responsive element 160 is held in place against, and if necessary electrically insulated from, conduit 120 by any suitable structure such as, for example, an insulating adhesive 192. Also as mentioned earlier, an additional temperature responsive element 162 may be placed directly inside the fluid path.

It should be noted that the present invention may be implemented using any suitable temperature sensing technology. Typically, electrical contact thermometer technology is used in which a temperature responsive element is deployed in contact with the object of which the temperature is to be measured. One typical but non-limiting example of a suitable technology is the use of a thermistor associated with suitable sensing circuitry. Other examples include, but are not limited to, thermoelectric thermometers, resistance thermometers, semiconductor thermometers, quartz thermometers, fiber optic thermometers, and ultrasonic thermometers. In an alternative set of implementations, optical pyrometers may be used.

FIG. 5B additionally illustrates the option of including an electrically insulating lining 179 within conduit 120.

According to another embodiment of the present invention, device 100 is lightweight and portable and easy to handle in all weather and environmental conditions. Device 100 is sterile and any parts coming in contact with the liquid are disposable.

According to certain preferred embodiments of the present invention, device 100 is activated under a operating voltage in the range of about 6V to 24V, and most preferably, no more than about 12V. Operation at these low, and therefore relatively safe, voltages is facilitated by the fact that the metallic material of conduit preferably has an electrical resistance of no more than about 15 ohms, and most preferably no more than about 5 ohms.

According to certain preferred embodiments of the present invention, the device may be activated by an external power source that is connected to the electric power mains, or to the external power source of a vehicle in the field.

According to another embodiment of the present invention, device 100 ensures a high functional and operational stability under mechanical and thermal shocks. This is primarily achieved by providing structural support for conduit 120.

According to another embodiment of the present invention, device 100 is fully functional and operational under extreme environmental conditions along with low power consumption and is adapted to be utilized in field environment such as emergency medical services, ambulances, flight service, watercraft service or military echelons and battlefield operations.

According to another embodiment of the present invention, device 100 includes a safety valve that can be activated to stop the fluid flow when an hazardous emergency case occurs. Controller 140 has additional safety features that allow momentary, temporary or constant fluid flow stops. The device also has a manual fail safe button that can be activated by the user.

According to another embodiment of the present invention, device 100 further includes an insulator (not shown) surrounding metal conduit 120 operative to electrically insulate metal conduit 120 as well as to behave as a temperature insulator. Thus, conduit 120 is inexpensive, easy to manufacture, and is suitable for use in a wide range of field environments.

According to another embodiment of the present invention, device 100 further includes a monitor operative to determine the presence of a fluid flow and to interrupt the device operation if the fluid flow has been stopped.

All references cited herein are incorporated by reference in their entirety. Citation of a reference does not constitute an admission that the reference is prior art.

The present invention has been described using detailed descriptions of embodiments thereof that are provided by way of example and are not intended to limit the scope of the invention other than as explicitly recited in the appended claims. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A device for heating a flow of liquid from an initial temperature to a desired temperature for intravenous delivery, the device comprising:
   (a) an elongated metal conduit having an inlet for receiving the flow of liquid at the initial temperature and an outlet for delivering the flow of liquid at the desired temperature, said metal conduit being in substantially direct thermal contact with the flow of liquid;

(b) at least one temperature sensing arrangement associated with said conduit and deployed to generate an output indicative of a temperature of the liquid at least one location along said conduit; and (c) a controller associated with said temperature sensing arrangement and deployed for generating electrical current flowing within at least one length of the wall of said metal conduit, thereby generating heat within said wall so as to heat the flow of liquid to reach the desired temperature at said outlet.

2. The device of claim 1, wherein said at least one temperature sensing arrangement includes a temperature responsive element positioned in thermal contact with an external surface of said conduit.

3. The device of claim 2, wherein said conduit has a minimum wall thickness of no more than about 1.4 mm.

4. The device of claim 2, wherein said conduit has a minimum wall thickness of no more than about 0.4 mm.

5. The device of claim 2, wherein said conduit is formed a material having a thermal conductivity of at least about 5 W/(m.K).

6. The device of claim 1, wherein said conduit has an electrical resistance of no more than about 15 ohms.

7. The device of claim 1, wherein said conduit has an electrical resistance of no more than about 5 ohms.

8. The device of claim 1, wherein said conduit is formed primarily from stainless steel.

9. The device of claim 1, wherein said controller is deployed for generating a first electrical current flowing within a first length of said wall of said conduit and a second electrical current flowing within a second length of said wall of said conduit.

10. The device of claim 9, wherein the fluid flow from said inlet to said outlet passes sequentially through said first length and said second length, and wherein said at least one temperature sensing arrangement is deployed to generate an output indicative of a temperature of the liquid:

(a) in proximity to a transition from said first length to said second length; and (b) after flowing through said second length.

11. The device of claim 10, wherein said controller is configured to generate said first current so as to heat the fluid flow passing along said first length through a majority of a temperature difference between the initial temperature and the desired temperature, and to generate said second current so as to heat the fluid flow passing along said second length through a remaining temperature correction to achieve the desired temperature at said outlet.

12. The device of claim 9, wherein said first length and said second length of said conduit are interconnected by an intermediate section of said conduit, and wherein said at least one temperature sensing arrangement includes a temperature responsive element positioned in thermal contact with an external surface of said intermediate section.

13. The device of claim 1, wherein said temperature sensing arrangement includes a temperature responsive element deployed within the liquid flow in proximity to said outlet.

14. The device of claim 1, wherein said conduit includes an internal coating of an electrically insulating layer.

15. The device of claim 1, wherein said conduit is provided with a thermally insulating covering over a major portion of its surface.

16. The device of claim 1, wherein said conduit, said at least one temperature sensing arrangement and said controller are included within a portable housing.

17. The device of claim 16, wherein said housing further includes a battery associated with said controller and configured to allow operation of the device without connection to an external power supply.

18. The device of claim 1, wherein said controller is implemented as a reusable device, and wherein at least said conduit is implemented as a single-use interchangeable element.

19. The device of claim 1, further comprising a flow meter associated with said controller and operative to measure a rate of the fluid flow through said conduit.

20. The device of claim 1, further comprising a flow pump associated with said controller and operative to generate a desired rate of the fluid flow through said conduit.

21. The device of claim 1, further comprising a flow shut-off valve associated with said controller and deployed to selectively shut off flow through said conduit.

* * * * *

UNITED STATES PATENT AND TRADEMARK OFFICE
CERTIFICATE OF CORRECTION

PATENT NO. : 8,079,981 B2
APPLICATION NO. : 12/870824
DATED : December 20, 2011
INVENTOR(S) : David Vishnia et al.

It is certified that error appears in the above-identified patent and that said Letters Patent is hereby corrected as shown below:

Column 11

Claim 1 line 5 should be
Change
-- put indicative of a temperature of the liquid at least one --
to
"put indicative of a temperature of the liquid at at least one"

Signed and Sealed this
Twenty-eighth Day of February, 2012

David J. Kappos
*Director of the United States Patent and Trademark Office*